United States Patent [19]

Hammar

[11] 4,326,532
[45] Apr. 27, 1982

[54] ANTITHROMBOGENIC ARTICLES

[75] Inventor: Walton J. Hammar, St. Paul, Minn.

[73] Assignee: Minnesota Mining and Manufacturing Company, St. Paul, Minn.

[21] Appl. No.: 194,576

[22] Filed: Oct. 6, 1980

[51] Int. Cl.³ .............. A61M 25/00; B01D 13/00; A01N 43/16
[52] U.S. Cl. .............. 128/349 R; 210/321.3; 424/183; 427/339; 427/419.7; 428/411; 428/473
[58] Field of Search .............. 128/1 R, 156, 213 A, 128/214 B, 214 D, 325, 348–350, DIG. 22; 210/321.3, 500.1, 500.2; 260/9; 424/16, 183; 428/411, 420, 423.1, 473; 427/339, 415, 419.7

[56] References Cited

U.S. PATENT DOCUMENTS

| | | | |
|---|---|---|---|
| 3,441,142 | 4/1969 | Oja .............. | 210/321.3 |
| 3,475,410 | 10/1969 | Britton . | |
| 3,755,218 | 8/1973 | Yen et al. .............. | 260/9 |
| 3,932,627 | 1/1976 | Margraf .............. | 424/183 |
| 4,265,927 | 5/1981 | Ericksson et al. .............. | 424/183 |
| 4,291,133 | 9/1981 | Horak et al. .............. | 424/183 |

OTHER PUBLICATIONS

Evans et al, *Thrombos. Haemostas.*, 41, 537 (1979).
Nakagima et al, *J. Colloid and Interface Sci.*, 55, No. 1, 126 (1976).
Kikuchi et al, *J. App. Poly. Sci.*, 20, 2561 (1976).
*Abstracts*, Kikuchi.

*Primary Examiner*—C. Fred Rosenbaum
*Attorney, Agent, or Firm*—Cruzan Alexander; Donald M. Sell; Lorraine R. Sherman

[57] ABSTRACT

A medical article having a layered antithrombogenic surface is useful as a polymeric implant. The article comprises a polymeric substrate coated with chitosan to which is appended an antithrombotic agent. A process for rendering the surface of a polymer antithrombogenic is disclosed.

18 Claims, No Drawings

ANTITHROMBOGENIC ARTICLES

TECHNICAL FIELD

This invention relates to formed polymeric structures and self-supporting films having antithrombogenic surfaces which are useful in the medical arts.

BACKGROUND ART

Medical articles having surfaces designed to prevent or inhibit thrombus formation are known in the art. The need for such surfaces has become increasingly important due to the common use of polymeric implants in areas of the body where contact with moving blood is required, e.g., heart, blood vessels. Numerous other medical articles formed from polymeric materials, such as catheters, tubing in heart-lung machines, and tubing and membranes in kidney dialysis machines require contact with blood. The contact sites on the surface of untreated polymeric articles are prone to thrombus formation due to improper protein deposition on the surface of the polymeric article and to platelet adhesion and subsequent aggregation. Such thrombi may serve as a source of emboli which are potentially life-threatening.

Heparin is known to prolong the clotting time of blood. Several techniques are described in the art for appending heparin to polymeric devices and films to reduce thrombus formation on the surfaces thereof. U.S. Pat. No. 3,441,142 discloses a permeable membrane wherein the alkali metal salt of heparin reacts with a polymer containing a quaternized nitrogen moiety. U.S. Pat. No. 3,755,218 discloses a nonthrombogenic reaction product between a polyquaternary polyurethane and heparin, and U.S. Pat. No. 3,932,627 teaches the heparinization of polymeric surfaces with a silver-heparin-allantoin complex. U.S. Pat. No. 3,475,410 discloses the amination of cellulose film and its subsequent heparinization to produce a nonthrombogenic surface thereon. R. Evans and others, Thrombos. Haemostas., 41, 537 (1979) disclose partial prevention of intravascular thrombus formation on plastic catheters surface-treated with a heparin-benzalkonium complex.

Although the heparin-treated surfaces described in the prior art are generally successful in reducing thrombus formation to some degree, there still existed, prior to the present invention, the need for an improved method of attaching an antithrombogenic agent to a polymeric surface which would substantially eliminate thrombus formation. According to the present invention, it has been discovered that by using an intermediate layer of chitosan to bond an antithrombotic agent such as heparin to the polymeric substrate, the surface exhibits surprisingly improved antithrombogenic character over other heparin-treated surfaces.

Chitosan complexes with heparin and other sulfated polysaccharides have been reported in the literature. Y. Kikuchi and A. Noda, J. of Applied Polymer Science, 20, 2561 (1976) have studied water-insoluble polyelectrolyte complexes of heparin with chitosan. The antithrombogenic character of the polyelectrolyte complexes is under investigation. A glycol chitosanheparin complex, stoichiometrically formed, is disclosed by A. Nakagima and K. Shinoda, J. of Colloid and Interface Science, 55, No. 1, 126 (1976), although no use is specified. Yasuo Kikuchi and Tatsuko Toyota, Hiroshima Daigaku Kogakubn Kenkyn Hokoku 24(2), 7-9 (1976), abstract available, CA 85: 10389C, disclose polyelectrolyte complexes of chitosan and sodium dextran sulfate, which, like heparin, is a sulfated polysaccharide, and which are antithrombogenic.

The above-mentioned complexes when formed are insoluble in water and common organic solvents and would not render themselves amenable to a coating process. Hence, the above-mentioned chitosan complexes and their methods of formation are different in character and not useful for preparing the layered composite structures disclosed herein which provide antithrombogenic surfaces to medical articles. Applicants rely on uncomplexed chitosan as a coating which is subsequently subjected to bonding with an antithrombogenic agent. Disclosed herein are composite structures which are blood compatible and which maintain their efficacy for longer periods of time than can be achieved with prior art materials.

SUMMARY OF THE INVENTION

In one aspect, this invention provides a medical article having a layered antithrombogenic surface comprising a polymeric substrate, a chitosan coating bonded to the polymeric substrate, and an antithrombotic agent bonded to the chitosan coating.

In another aspect, this invention provides a process for rendering the surface of a polymer antithrombogenic by priming the non-hydrophilic polymeric surface so as to make it receptive to the coating of a chitosan salt thereon, coating a chitosan salt from acid solution having a pH of about 6 or less onto the polymeric surface, reacting the resulting chitosan salt-coated polymeric surface with base to convert the chitosan salt to free chitosan, and bonding an antithrombogenic agent to the chitosan-coated polymeric article.

A yet further aspect of this invention provides a self-supporting film of chitosan with an antithrombotic agent covalently or ionically bonded thereto.

Chitosan is prepared from chitin, a substance that forms part of the outer integument of insects and crustaceans, and is defined (Merck Index, 8th Edition) as a polysaccharide consisting predominantly of unbranched chains of $\beta$-(1→4)-2-acetamido-2-deoxy-D-glucose residues. Chitin is regarded as a derivative of cellulose, in which the C-2 hydroxyl groups have been replaced by acetamido residues and resembles cellulose in many of its properties. Chitosan is prepared from chitin by partial deacetylation with alkali. Chitosan is defined herein to mean chitosan as well as its lower N-alkyl ($C_1$ to $C_4$) derivatives thereof.

The polymeric substrates of the present invention may be either natural or synthetic structures. Particularly useful are structures made of cellulose, polyethylene, polyvinyl chloride, polyurethane, polypropylene, teflon, or silicone rubber.

"Antithrombotic", "nonthrombogenic", and "blood-compatible" are used interchangeably herein to refer to any material which inhibits thrombus formation on a surface by mechanisms such as reducing platelet aggregation thereon or releasing anticoagulant into surrounding media.

DETAILED DESCRIPTION

The present invention provides a layered medical article having an antithrombogenic surface comprising a natural or synthetic primed polymeric substrate such as polyethylene, polyvinyl chloride, teflon, silicone rubber, or cellulose; a layer of chitosan bonded to the primed substrate; and a layer of antithrombogenic agent such as heparin, prostaglandin, dextran sulfate, or albumin bonded to the chitosan layer. A critical element in the layered composite herein described is the placement of the natural polymer, chitosan, between a medical article constructed of polymeric material and an antithrombogenic agent. In the instant invention, there is no stoichiometric relationship between chitosan and the antithrombogenic agent, since the chitosan is only surface-treated with heparin or other antithrombogenic agent.

The levels of chitosan and heparin in their respective layers is from about 0.01 to about 100 mg/cm$^2$ and about 0.1 to about 7.0 I.U.'s/cm$^2$ (International Units of activity). Preferably the level of chitosan is from about 0.05 to about 1.0 mg/cm$^2$ and the most preferred level is about 0.1 mg/cm$^2$. Optimum levels of other antithrombogenic agents useful in the present invention (e.g., see EXAMPLES 8 and 9) may be determined empirically. The procedures for forming the composites are more fully illustrated in the EXAMPLES below. In general, the polymeric surface of an article is first primed. Priming is accomplished by one of three methods: (1) with oxygen $R_f$ plasma discharge; (2) chromic acid oxidation; or (3) $R_f$ plasma polymerization of acids on the surface. Priming facilitates the bonding of chitosan to the polymer by introducing polar groups on the polymeric surface to which the chitosan subsequently can be covalently bonded (see EXAMPLE 3). Ionic bonding of chitosan to the polymer is achieved by neutralization of the chitosan acetic acid salt coated thereon (see EXAMPLE 4). The antithrombogenic agent, preferably heparin, is then bonded to the chitosan by ionic adsorption as in EXAMPLE 5, or by covalent bonding, using boron hydrides, as in EXAMPLE 6. There is evidence that 0.1 to 5% solutions of NaBH$_4$ or NaCNBH$_3$ reduce the Schiff's base formed by the reaction of the hemiacetal group of heparin and the amine group of chitosan, forming a covalent bond joining the heparin to chitosan. Covalently-bonded heparin exhibits very little leaching from the surface even in the presence of a concentrated saline (25%) solution. Alternately, glutaraldehyde may be used to form a crosslinked glutaraldehyde/chitosan/heparin surface, as described in EXAMPLE 7. This is another method of attaching heparin to chitosan and results in slower release of heparin from the coated surface than is obtained with ionically-bonded heparin to chitosan surfaces, as shown by in vivo animal experiments.

The resulting composites were then tested for surface thrombogenicity and blood platelet adhesion. The procedures and results of this biological testing are given below in detail.

DETERMINATION OF SURFACE THROMBOGENICITY OF VARIOUS MATERIALS IN THE CANINE AND SWINE ARTERIAL SYSTEM

The protocol for this study arose as a modification of a similar test employed by the Utah Biomedical Testing Laboratory, Salt Lake City, Utah. It was desired to obtain a rapid subjective and quantitative method to screen various catheters and coating materials on catheters for thrombogenicity in an in vivo system. Promising antithrombogenic materials could then be subjected to more strenuous tests to prove antithrombogenicity and non-embolization. The test in itself was more severe than ordinary catheter use.

Adult Beagle dogs of either sex, weighing greater than 10 kg, or young swine, weighing greater than 20 kg, were used for each individual study. Dogs and pigs were selected as the test subjects for this experiment because of their size. Dogs are further preferred because their blood is known to be hypercoagulative.

The catheters to be implanted were approximately 15 cm long and 5 French (1.67 mm) o.d. At least the terminal 10 cm of the test catheters were coated with a test material presumed to be antithrombogenic. A total of 48 catheters randomized among three animals were tested at each evaluation time. At least 12 of the 48 catheters were of control material that was presumed to be thrombogenic. Identification as to control or test material was retained by the sponsor. The catheters were clean but generally not sterile. In cases where catheters were sterilized, ethylene oxide was used followed by the catheters being placed in an aeration chamber for at least 16 hours. Catheters were implanted into the carotid and femoral arteries of each animal.

Prothrombin time, partial thromboplastin time, and fibrinogen levels of the animals were determined prior to surgery. All laboratory tests had to fall within normal limits for the animal to be acceptable for its use in the test procedure. All animals were fasted at least 16 hours before surgery and pre-anesthetized with acetylpromazine maleate and atropine sulfate. The pigs were later immobilized with ketamine hydrochloride.

Anesthesia was induced with intravenous pentobarbitol sodium given to effect and maintained following endotracheal intubation with incremental doses of the barbiturate as needed. The hair from both groin areas and the entire neck was closely shaved. No preparation for aseptic surgery was performed as the study was an acute experiment. The animals were placed in dorsal recumbency and the external jugular vein in each dog and the internal jugular vein in each pig exposed. A commercial indwelling catheter was placed in this vein for administration of lactated Ringer's solution, further anesthetic injections, and the periodic withdrawal of blood samples. The right and left carotid and right and left femoral arteries were exposed at sites located so that inserted catheters would not touch one another during the test. The proximal portion was temporarily ligated with a silicone rubber band. Approximately 2 cm distal to the temporary ligation, the artery was totally ligated with a 3-0 silk suture. The intervening 1 cm was incised longitudinally and a single interrupted stitch of 6-0 suture material was placed on each side of the arteriotomy. The ends of the suture were left long and clamped with a hemostat to maintain the arteriotomy opening as wide as possible. Blood samples were taken for measurement of the above parameters after exposure of all four of the arteries in all three animals. Approximately 154 microcuries of I$^{125}$ labeled human fibrinogen was then injected intravenously. In some trials, previously collected platelets from the same animals were also labeled with In$^{111}$ and injected at this time to determine any platelet aggregation on the surface of the material that did not necessarily result in thrombus initiation. Approximately five minutes later, another blood sample was taken to determine the radioactivity/ml of blood. Blood samples were taken at least at the beginning of the experiment and at the end and in some instances were taken every half hour for measurement of the above parameters. Occasionally blood samples were taken for heparin content.

Four catheters were inserted into each artery sequentially for about 30 minutes each. The interior of the catheter was not evaluated in this test and, therefore, the end was clamped with a hemostat before insertion into the artery. The catheter was inserted past the rubber band proximally a distance of about 10 cm. A hemostat was used to clamp the rubber band snugly around the catheter. When the catheter was removed, the rubber band was released and blood was allowed to gush from the artery a few seconds to flush out any clots not adherent to the catheter. The catheter was dipped once in normal saline after removal from the artery and flushed once with at least 10 cc of normal saline before determining the amount of thrombus on its surface. The amount of adherent thrombus and the amount extruded were assessed visually on a scale of 0–5 (1 for each 2 cm of clot). Some consideration was also given to its thickness. Note was made of where the thrombus, if any, was located since the proximal and distal sections were in a somewhat different hemodynamic environment because of the occlusion of the blood vessel at the arteriotomy site. The catheter was cut in half and placed in radioactive counting vials. Any extruded clot was placed in the same vial. The radioactivity of the entire catheter and extruded thrombus was determined at a later date. A second test catheter was then inserted into the artery by the same technique utilized for the first. This procedure was continued through the arteries mentioned above and all catheters to be evaluated in those animals. At the conclusion of the testing, the animal was sacrificed. Differences in thrombus initiation by the catheters was evaluated statistically by mean and standard deviations of total scores or ranked sums of each catheter type.

The results of a variety of surfaces tested are illustrated in TABLE I. The data are listed in several ways: first, the total visual score of thrombus formation summed for all 12 catheters, second, the fraction of catheters which exhibit a thrombus either on the surface or in the artery, and third, the mean and standard errors of both the visual data and radiochemical ($I^{125}$ fibrinogen) data.

TABLE I

Results of Catheter Assays (in vivo data)

| Surface Material | Total Visual Score | Fraction w/Clots | Mean and Standard Error Visual Score | Mean and Standard Error Radiochem. Data[9] |
|---|---|---|---|---|
| Polyethylene | 31.5 | 12/12 | 2.63 ± 0.43 | 27,600 ± 5,630 |
| Polyvinyl chloride | 23.0 | 11/12 | 1.92 ± 0.36 | 21,250 ± 4,780 |
| Chitosan/heparin[1] | 0.0 | 0/12 | 0 ± 0 | 164 ± 19 |
| Chitosan/heparin/NaCNBH$_3$[1,11] | 3.0 | 6/12 | 0.25 ± 0.26 | 4,450 ± 3,420 |
| Chitosan/heparin/NaCNBH$_3$[1,2,11] | 0 | 0/12 | 0 ± 0 | 431 ± 89 |
| Chitosan/heparin/glutaraldehyde[1] | 2.0 | 4/12 | 0.17 ± 0.07 | 890 ± 123 |
| TDMAC/heparin[3] | 16.0 | 7/12 | 1.33 ± 0.38 | 17,680 ± 7.050 |
| Chitosan/chondroiton sulfate[1] | 3.5 | 3/12 | 0.29 ± 0.16 | 2,070 ± 1,340 |
| Chitosan/inulin sulfate[1] | 2.5 | 3/12 | 0.21 ± 0.11 | 647 ± 435 |
| Chitosan/dextran sulfate[1,4] | 3.0 | 1/12 | 0.25 ± 0.25 | 5,610 ± 5,514 |
| Toray commercial catheter[5] | 12.0 | 7/12 | 1.00 ± 0.34 | 11,740 ± 4,240 |
| Heparin/hexadecylamine[6] | 11.0 | 5/11 | 1.00 ± 0.41 | 9,350 ± 4,110 |
| Chitosan/heparin[7] | 0.0 | 0/12 | 0 ± 0 | 109 ± 12 |
| Teflon[8] | 15.0 | 14/16 | 1.22 ± 0.80 | |
| Albumin/chitosan | 8.5 | 6/12 | 0.21 ± 0.24 | |
| Prostaglandin E$_1$/chitosan | 4.25 | 3/12 | 0.35 ± 0.25 | |
| Chitosan/low mol. wt./heparin[10] | 0.2 | 1/12 | 0.06 ± 0.02 | |
| Dimethylchitosan/heparin | 10.0 | 4/12 | 1.35 ± 0.39 | |

[1] Coated on polyethylene
[2] After coating, the catheters were rinsed in 25% saline solution for 15 min.
[3] On polyethylene according to method G. A. Gode, R. D. Falb and J. P. Crowley, J.Biomed. Materials Res. Symposium #3, 77 (1972)
[4] Dextran sulfate molecular weight is 500,000
[5] A heparinized catheter obtained from Toray Industries, Japan, and called Anthron-I ®
[6] A heparinization treatment on polyethylene described by H. R. Lagerren and J. C. Eriksson, Trans. Amer. Soc. Artif. Org. 17, 10 (1971)
[7] Coated on polyvinyl chloride
[8] Larger nos. of catheters were studied in which radiochemical data is not directly comparable to rest of data
[9] Counts/min
[10] Heparin molecular weight was in the range of 6,000 Daltons
[11] Heparin was covalently bonded to chitosan using NaCNBH$_3$ The data show that chitosan/heparin performed very well as an antithrombogenic surface compared to untreated plastics such as polyethylene, polyvinyl chloride, and Teflon ®. Of particular importance was its superior activity compared to a variety of heparinized surfaces: heparin adsorbed and crosslinked onto hexadecylamine embedded in polyethylene, Toray Industries' antithrombogenic catheter (Anthron-I), and TDMAC (tridodecylmethylammonium chloride/heparin complex). Chemically bonding the heparin to chitosan using NaCNBH$_3$ also gave a surface which showed good antithrombogenicity. In addition, rinsing this surface with 25% NaCl solution (which had been demonstrated to remove all unbound heparin) still left an excellent antithrombogenic surface with heparin covalently bonded. Other sulfated polysaccharides such as dextran sulfate, chondroitin sulfate and inulin sulfate demonstrated good blood compatibility compared to reference plastics.

Platelet adhesion studies using platelet-rich plasma were run using the Chandler loop model (A. B. Chandler, Lab. Investigations, 1, 110 (1958)) to determine the amount of platelets adhered to the surface in μg of platelet protein/cm$^2$ (monitored using In$^{111}$ labeled platelets). The resultant data are listed in TABLE II and indicate that chitosan surfaces alone exhibited a surprising and marked reduction in the adhesion of platelets. With heparin also present, platelet adhesion was further reduced.

TABLE II

Platelet Adhesion Studies (in vitro data)

| Material | Platelet Adhesion Mean ± Standard Error for μg Platelet Protein/cm$^2$ |
|---|---|
| Polyethylene | 8.1 ± 0.8 |
| Polyvinyl chloride | 6.6 ± 0.2 |
| Chitosan | 0.6 ± 0.1 |
| Chitosan/heparin | 0.4 ± 0.1 |

In another trial using the in vivo catheter assay model described above, chitosan surfaces alone did not demonstrate antithrombogenic character. Thus, the presence of heparin was also required. However, NaCNCH$_3$ can be used to cause the formation of a strong covalent bond between chitosan and heparin resulting in a relatively permanent antithrombogenic surface (see TABLE I.)

TABLE III

Results of Catheter Assays (in vivo data)

| Material | Total Visual Score | Fraction w/Clots | Mean ± Standard Error Visual Score | Radiochem.Data |
|---|---|---|---|---|
| Polyethylene | 11.0 | 14/24 | 0.46 ± 0.11 | 1,200 ± 308 |
| Chitosan on polyethylene | 15.0 | 11/24 | 0.62 ± 0.24 | 4,330 ± 2,010 |
| Chitosan/heparin on polyethylene* | 0.0 | 0/12 | 0 ± 0 | 164 ± 19 |

*Data from Table I

The data of TABLE III confirm the superior antithrombogenic properties of a chitosan/heparin coating on polyethylene compared to uncoated polyethylene or chitosan coated polyethylene.

It is clearly envisioned and within the scope of this invention that other useful and compatible additives may be incorporated in the antithrombogenic surfaces of this invention, for example, silver salts for antimicrobial activity.

Objects and advantages of this invention are further illustrated by the following examples, but the particular materials and amounts thereof recited in these examples, as well as other conditions and details, should not be construed to unduly limit this invention.

EXAMPLE 1—Oxygen R$_f$ plasma priming of polymer surface

The article to be coated was placed in a chamber attached to a vacuum line and an oxygen source. The chamber was also fitted with the proper electrical equipment to deliver radiofrequency radiation (13.56 MHz at 50–500 watts), either in a capacitance or inductive mode. The chamber was evacuated and filled wth oxygen. This process was repeated a total of three times. The chamber was then evacuated to 0.1–1.0 mm of Hg and power of 50–500 watts was turned on for a time ranging from 10 seconds to 2 minutes. The article surface was then wettable and was readily coated according to procedures outlined below.

EXAMPLE 2—R$_f$ plasma polymerization of acrylic acid onto silicone rubber surface A silicone rubber article was placed in the chamber as described in EXAMPLE 1. Instead of introducing oxygen at the inlet, acrylic acid vapors were allowed to enter the chamber. After proper evacuation and filling, the chamber pressure was adjusted to 0.1–1.0 mm of Hg with acrylic acid vapors present. The radiofrequency power (50–500 watts, 200 watts optimum) was turned on and continued for a period of 1–10 minutes (2 minutes optimum). The article was then removed from the chamber and coated with chitosan either with or without first treating with a carbodiimide (see EXAMPLE 3).

EXAMPLE 3—Covalent attachment of chitosan salt to a polymer containing surface carboxyl groups The primed polymeric article was allowed to stand in a 0.6% aqueous solution of 1-ethyl-3-(3-dimethylaminopropyl)-carbodiimide hydrochloride at pH 4.0 for 20 hours. The article was then dip-coated in a 0.6% chitosan solution (4 g chitosan, 3 g acetic acid and 600 cc H$_2$O). The article was dried in air and placed in a pH 10 buffer solution for 20 hours.

EXAMPLE 4—Ionic attachment of chitosan to a polymeric article

Polypropylene which has been oxygen R$_f$ plasma treated (EXAMPLE 1) was dip-coated in a 0.6% chitosan in 1% acetic acid solution. The article was then air dried. The chitosan acetic acid salt on the surface was then treated with 1 M NH$_4$OH solution to convert to chitosan free base. The article was then rinsed several times with distilled water to remove excess NH$_4$OH.

EXAMPLE 5—Heparinization of a chitosan coated article (ionic adsorption)

The chitosan-coated article was soaked in 1% U.S.P. sodium heparin in pH 7.0 0.2 M phosphate buffer for 1–20 hours (preferably about 3 hours). The article was removed and rinsed thoroughly with distilled water.

EXAMPLE 6—Heparinization of chitosan coated article using boron hydrides

After heparinization, the article from EXAMPLE 5 was allowed to react with 0.3% NaBH$_4$ solution in 0.2 M phosphate buffer at pH between 7–10 for 1–24 hours. The article was removed from the heparin solution and thoroughly rinsed with distilled water.

Alternatively, the chitosan-coated article was placed in a pH 7.0 0.2 M phosphate buffer containing 1% U.S.P. heparin and 1% NaCNBH$_3$ for a period of three hours. The sample was removed and rinsed thoroughly with distilled water.

It is believed that the use of NaBH$_4$ or NaCNBH$_3$ covalently binds the hemiacetal of heparin to the amine of chitosan resulting in a material surface from which heparin is not lost even using strong saline (25%) solution.

EXAMPLE 7—Crosslinking of chitosan/heparin surface with glutaraldehyde

Chitosan/heparin-coated material was placed in a 0.1–0.4% glutaraldehyde (freshly distilled) aqueous solution for 5–15 minutes at 55° C. The sample was removed and thoroughly rinsed with distilled water. In vivo animal experiments demonstrated that heparin leached at a much slower rate from this surface than from an uncrosslinked material (EXAMPLE 5). However, 25% NaCl solution completely removed heparin (observed by staining techniques and ATR-IR) from this glutaraldehyde crosslinked surface. This represents an alternative method of attaching heparin to chitosan and resulted in a slower release of heparin compared to surfaces to which it was ionically bonded (EXAMPLE 5) but not as slow release as on surface to which it is believed to be covalently bonded (EXAMPLE 6).

EXAMPLE 8—Chitosan/Prostaglandin $E_1$ surface

The chitosan-coated article was allowed to soak for two hours in 0.05% prostaglandin solution in methanol under a nitrogen purge. The article was then dried and rinsed in a water solution for 30 minutes and then again allowed to dry.

EXAMPLE 9—Chitosan/albumin surface

The chitosan coated article was allowed to soak for three hours at room temperature in a 5% albumin solution (pH 7.0, 0.2 M phosphate buffer). The article was removed and rinsed with distilled water and allowed to dry.

EXAMPLE 10—Preparation of dimethylchitosan

Chitosan (8.0 g, 50 mmoles based on glucosamine) was dissolved in 400 cc of water containing 3.3 g of glacial acetic acid. Formalin solution (40 ml, 500 mmoles formaldehyde) was added. A solution of $NaCNBH_3$ (9.5 g, 150 mmoles) in 70 cc of water was added followed by addition of 5 cc of glacial acetic acid. The reaction mixture was stirred at ambient temperatures for 20 hours and then basified by addition of 300 cc of water containing 7.0 g KOH. The solid was collected, thoroughly rinsed with water, purified by redissolving in acetic acid solution, and then precipitated with KOH. The precipitate was rinsed thoroughly with water until the filtrate was neutral. Nmr data are consistent for a structure involving two methyl groups on the nitrogen of each glucosamine unit.

EXAMPLE 11—Dimethylchitosan/heparin surface

The polymeric article (properly primed, e.g., see EXAMPLES 1 and 2) was dip coated in a 0.6% dimethylchitosan solution (1% acetic acid). The coated article was allowed to dry and then immersed in a 1 M $NH_4OH$ solution for 20 minutes. The article was then thoroughly rinsed with water and allowed to soak for three hours in a 1% sodium heparin solution (pH 7.0, 0.2 M sodium phosphate buffer). The heparinized article was then rinsed with water and allowed to air dry.

EXAMPLE 12—Heparinization of a self-supporting chitosan film

A chitosan film was prepared by coating onto unprimed polypropylene a 2% solution of chitosan in 1% acetic acid in water. Several coatings were required to obtain the desired thickness of chitosan of about 50 to about 250 microns, with the preferred thickness being about 100 to about 150 microns. The dried film was readily peeled and was then immersed in a 1% sodium heparin solution (pH 7.0, 0.2 M sodium phosphate buffer) at room temperature for 20 hours. The film was removed and rinsed thoroughly with distilled water. Staining with toluidene blue and IR analysis gave evidence of the presence of heparin in the film. It is anticipated that these films will find use in heart-lung machines, left ventricular assist devices, and heart valves.

Various modifications and alterations of this invention will become apparent to those skilled in the art without departing from the scope and spirit of this invention, and it should be understood that this invention is not to be unduly limited to the illustrative embodiments set forth herein.

We claim:

1. A medical article of manufacture having a layered nonthrombogenic surface comprising:
   a natural or synthetic polymeric substrate,
   a chitosan coating bonded to said polymeric substrate, and
   an antithrombotic agent bonded to said chitosan coating.

2. The article according to claim 1 wherein said antithrombotic agent is a sulfated polysaccharide, prostaglandin, or albumin.

3. The article according to claim 2 wherein said antithrombotic agent is heparin.

4. The article according to claim 1 wherein said polymeric substrate is a catheter.

5. The article according to claim 1 wherein said polymeric substrate is a kidney dialysis membrane.

6. The article according to claim 1 wherein said polymeric substrate is silicone rubber, polyethylene, polyvinyl chloride, polyurethane, polypropylene, teflon, or cellulose.

7. The article according to claim 1 wherein the level of chitosan in said chitosan coating is in the range of about 0.01 to 100 $mg/cm^2$.

8. The article according to claim 7 wherein said level of chitosan in the chitosan coating is about 0.05 to 1.0 $mg/cm^2$.

9. The article according to claim 3 wherein the level of heparin is in the range of about 0.1 to 7.0 I.U.'s/$cm^2$.

10. A process for rendering the surface of a polymer antithrombogenic comprising the steps:
    (a) priming said polymeric surface so as to render it receptive to the coating of a chitosan salt thereon,
    (b) coating said chitosan salt from acid solution onto said polymeric surface,
    (c) reacting the resulting chitosan salt coated polymeric surface with base to convert said chitosan salt to free chitosan, and
    (d) bonding an antithrombogenic agent to said chitosan coated polymeric article.

11. A process according to claim 10 further comprising bonding said chitosan coated polymeric article with said antithrombogenic agent in the presence of a chemically effective amount of a boron hydride.

12. A process according to claim 11 wherein said boron hydride is $NaBH_4$ or $NaCNBH_3$.

13. A process according to claim 10 further comprising treating the resulting antithrombogenic article with glutaraldehyde to crosslink the chitosan and antithrombogenic agent.

14. The process according to claim 10 wherein said chitosan coating is covalently bonded to said polymeric substrate.

15. The process according to claim 10 wherein said chitosan coating is ionically bonded to said polymeric substrate.

16. The process according to claim 10 wherein said antithrombotic agent is covalently bonded to said chitosan coating.

17. The process according to claim 10 wherein said antithrombotic agent is ionically bonded to said chitosan coating.

18. An article of manufacture comprising a self-supporting film of chitosan with an antithrombotic agent bonded thereto.

* * * * *

UNITED STATES PATENT AND TRADEMARK OFFICE
CERTIFICATE OF CORRECTION

PATENT NO. : 4,326,532
DATED : April 27, 1982
INVENTOR(S) : Walton J. Hammar

It is certified that error appears in the above—identified patent and that said Letters Patent is hereby corrected as shown below:

Column 6, TABLE I, line 4 under subheading Radiochem. Data$^{(9)}$, replace "4,450 $\pm$ 3,420" with --4,540 $\pm$ 3,420--.

Column 6, TABLE I, footnote (6), replace "Lagerren" with --Lagergren--.

Signed and Sealed this

Thirty-first Day of August 1982

[SEAL]

Attest:

Attesting Officer

GERALD J. MOSSINGHOFF

Commissioner of Patents and Trademarks